United States Patent [19]
Raybuck et al.

[11] Patent Number: 5,833,927
[45] Date of Patent: *Nov. 10, 1998

[54] DEVICE AND METHOD FOR AFFINITY SEPARATION

[75] Inventors: Margaret Patricia Raybuck, Pontyclun; Michael Kenneth Kenrick, Cardiff, both of Wales; David Alun Parry, London, England

[73] Assignee: Amersham International plc, United Kingdom

[ * ] Notice: The term of this patent shall not extend beyond the expiration date of Pat. No. 5,556,598.

[21] Appl. No.: 677,114

[22] Filed: Jul. 9, 1996

Related U.S. Application Data

[62] Division of Ser. No. 119,649, Sep. 13, 1993, Pat. No. 5,556,598.

[30] Foreign Application Priority Data

Sep. 18, 1992 [EP] European Pat. Off. ......... 92 308 536.9

[51] Int. Cl.⁶ ........................................... B01L 3/02
[52] U.S. Cl. ..................... 422/101; 210/460; 210/502.1; 422/100; 422/102; 435/287.2; 435/287.6; 435/308.1; 435/309.1; 436/518
[58] Field of Search ..................... 422/100, 101, 422/102; 210/502.1, 460; 436/518; 435/287.2, 287.6, 308.1, 309.1

[56] References Cited

U.S. PATENT DOCUMENTS

| | | |
|---|---|---|
| 3,985,032 | 10/1976 | Avakian . |
| 4,014,653 | 3/1977 | Gianos et al. . |
| 4,059,020 | 11/1977 | Avakian . |
| 4,267,729 | 5/1981 | Eddleman et al. . |
| 4,774,058 | 9/1988 | Mehl . |
| 4,787,971 | 11/1988 | Donald . |
| 4,795,562 | 1/1989 | Walsh . |
| 4,797,260 | 1/1989 | Parker . |
| 4,886,836 | 12/1989 | Gsell . |
| 4,933,148 | 6/1990 | Perlman . |
| 4,999,164 | 3/1991 | Puchinger . |
| 5,043,082 | 8/1991 | Hermann, Jr. et al. . |
| 5,079,170 | 1/1992 | Rosman . |
| 5,108,704 | 4/1992 | Bowers et al. . |
| 5,124,041 | 6/1992 | Sheer et al. . |
| 5,143,627 | 9/1992 | Lapidus et al. . |
| 5,156,811 | 10/1992 | White . |
| 5,171,537 | 12/1992 | Wainwright et al. . |
| 5,208,161 | 5/1993 | Saunders et al. . |
| 5,219,529 | 6/1993 | Ngo et al. . |
| 5,240,862 | 8/1993 | Koenhen et al. . |
| 5,556,598 | 9/1996 | Raybuck et al. ................... 422/100 |

FOREIGN PATENT DOCUMENTS

| | | |
|---|---|---|
| 0 198 413 | 10/1986 | European Pat. Off. . |
| 0 312 394 | 4/1989 | European Pat. Off. . |
| 2580074 | 10/1986 | France . |
| 86/03589 | 6/1986 | WIPO . |
| 88/09201 | 12/1988 | WIPO . |

OTHER PUBLICATIONS

*Webster's Ninth New Collegiate Dictionary*, Merriam Webster, Inc. (1990).
*Fisher Scientific Catalog*, p. 1508 (1988).

Primary Examiner—Jan Ludlow
Attorney, Agent, or Firm—Wenderoth, Lind & Ponack, L.L.P.

[57] ABSTRACT

A device for capturing a component present in a fluid is a pipette tip having a rearward end 15 adapted to be fitted on a micro-pipette, and a forward end 12 with a membrane 17, adapted to bind the component, extending across the pipette tip.

10 Claims, 3 Drawing Sheets

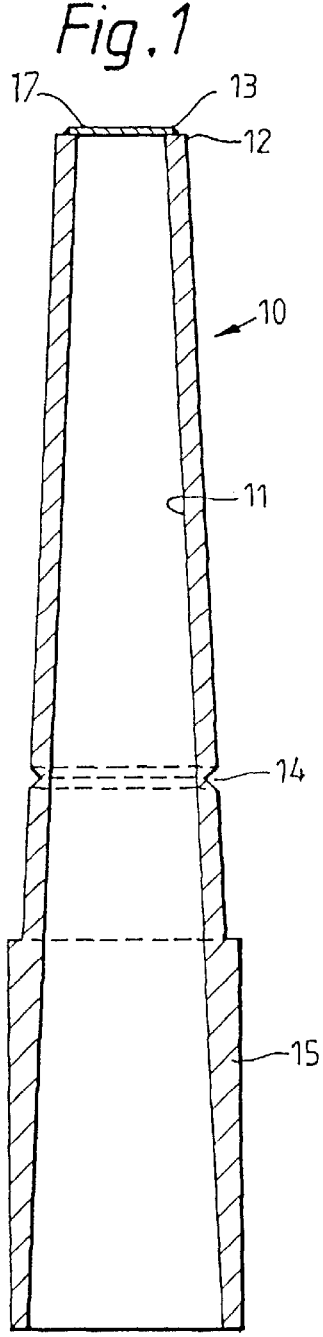
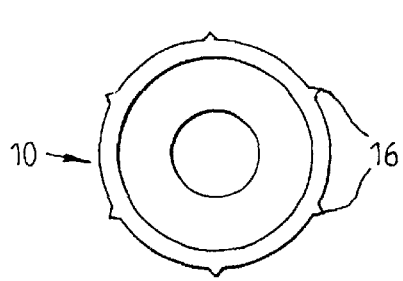
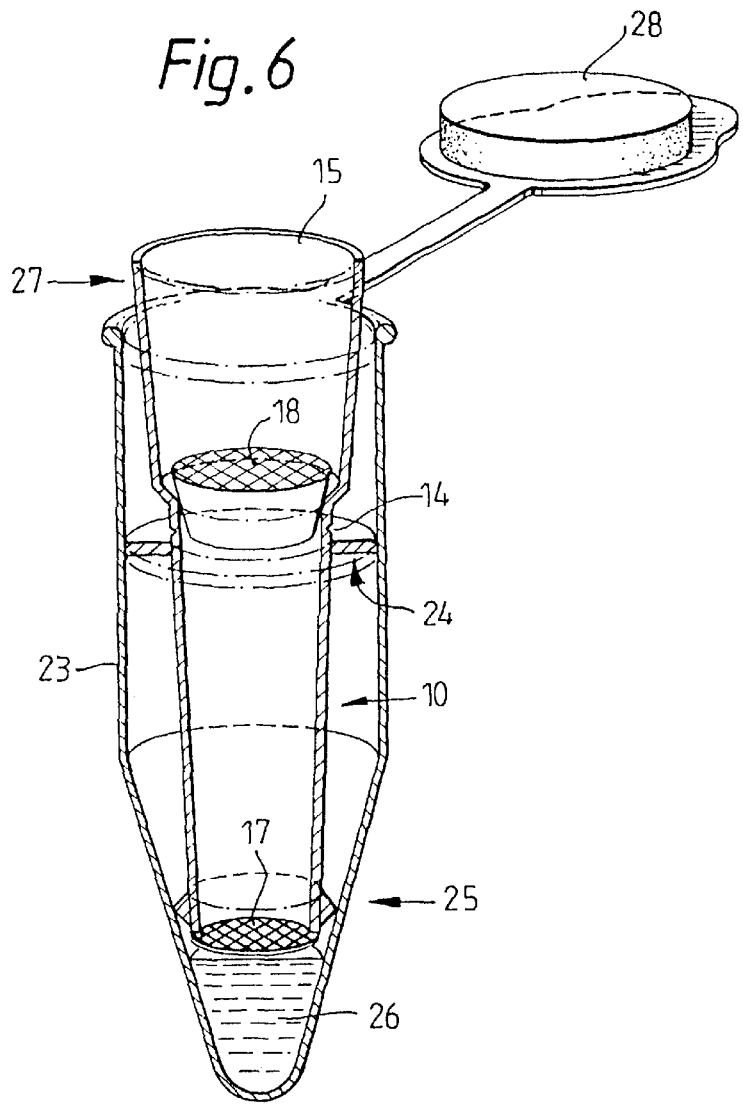

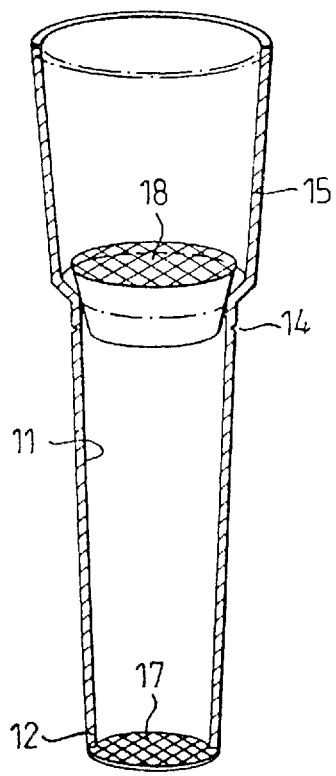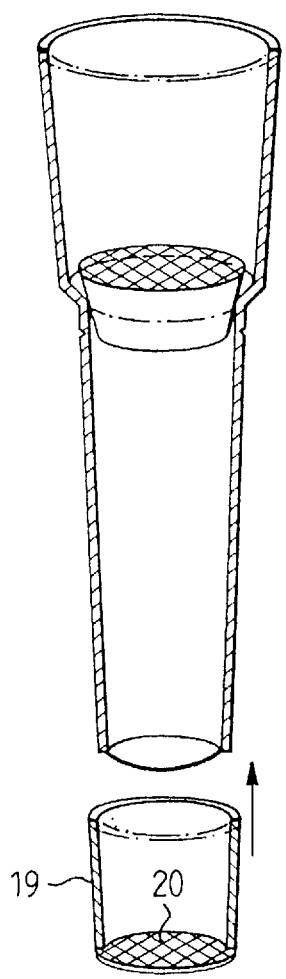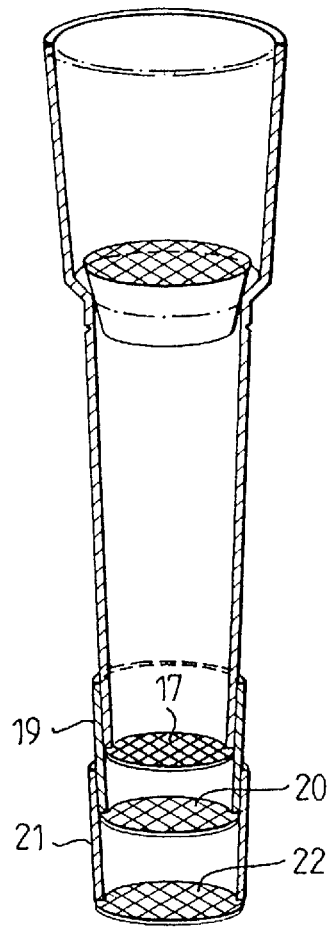

DEVICE AND METHOD FOR AFFINITY SEPARATION

This is a divisional application of Ser. No. 08/119,649, filed Sep. 13, 1993 now U.S. Pat. No. 5,556,598.

BACKGROUND

Separation processes are used widely in biological science to isolate one component from complex mixtures using a single or combination of unique characteristics of the desired entity. These characteristics can be size, shape, charge, hydrophobicity, solubility, density etc. all coming into the categorisation of chromatography. Usually these characteristics are not totally unique and so a series of different sequential separations must usually be taken to refine the purification. Often the choice of which steps to use is empirically determined and devising a new purification route is very laborious, each choice having many variants within it. The labile nature of many biological substances also makes this a difficult procedure, the desired substance sometimes decaying as fast as it can be purified.

A variant of these techniques is affinity chromatography. In this a more specific characteristic of the desired item is utilised in the separation strategy. Usually this involves a specific binding capability which is instrumental in effecting the separation. Biological systems employ specific binding very regularly as part of their natural functioning, such as in antibody/antigen interactions in disease resistance, or receptor/ligand interactions for cell signalling. This can be harnessed in a separation technique to obtain 100% separation in one step and is therefore a particularly powerful method. With such a powerful separation method it is important when performing these activities that all contaminating unbound materials are removed with high efficiency. Preferably there should be 100% efficiency both of contaminant removal and of capture of desired substance in the first pass. This requires maximal interaction between the desired substance or entity with its binding partner as well as very efficient washing.

A method is therefore needed where sufficient capture molecules to capture all the target molecules are held on a solid phase. This is done in such a way that the target molecule or entity has easy access to the binding site but also so that non-binding moieties can be washed off vigorously without trapping or spuriously interacting.

There are many formats for performing affinity chromatography procedures. All of them share the general feature of having one side of the binding pair immobilised to a solid phase. This most commonly consists of a bead material sometimes packed into columns. The liquid containing the desired entity can then flow over, around and in some cases inside the beads coming into contact with the capture entity and contaminants can then be washed by allowing washing solutions to flow over the bead surfaces. The stringency of the washing procedure can be influenced by the nature of the washing solution such as by temperature, ionic strength, pH, solvent mix etc.

Beads are in many cases a preferred option as this format maximises the surface on which the capture entity is immobilised.

In general the major requirement is for an insoluble material to which the capture entity can be attached such that a fluid containing the target be passed over the solid phase to allow maximum contact between the compartments. Also the solid phase normally requires a maximal surface area to allow sufficient capture entity to be available. In most cases the purpose of the procedure is for the removal of the target from a complex mixture in pure form and then elution of the target from the capture entity without the capture entity also being removed. For this to be possible conditions have to be found where the binding forces can be overcome without damage to either binding partners.

In recent times, especially in molecular biology, techniques have arisen which are manyfold more sensitive than before and so do not need such large amounts of sample as starting material. Also more and more of subsequent treatments are able to be done while still attached to the solid phase. This is the basis of the burgeoning fields of downstream processing and biotransformations where chemical modifications are made often enzymically by materials held on a solid phase.

There have appeared in the last few years several new formats for affinity chromatography based on filtration membranes especially for antibody purification. Most commonly these involve the use of a filtration cartridge format, familiar to those working in biological fields. This consists of either a disposable or reusable cassette within which is mounted a disc of filtration membrane.

The membrane is supported on both sides by plastic meshes within the cassette and leading out from the upper and lower surfaces of the cassette is a nozzle designed to be attached to a syringe and an outlet designed to be directed into the collection vessel. These cassettes sometimes include in the design, channels of liquid flow to maximise the interaction of the fluid across the membrane (U.S. Pat. No. 4,690,757).

Later developments have lead to new versions with either capture moieties already permanently attached or in a chemically activated form for custom derivatisation. The discs are usually about 5 cm in diameter and are claimed to have as high a binding capacity as a column. This is consistent with their use with a syringe for the application of large samples of between 1 and 50 mls of solution at a time.

As mentioned earlier the trend now is towards smaller samples, more sensitive detection and amplification techniques especially in molecular biology. In biology large samples are difficult to obtain and involve significant derangement to the biological entity which is the source of the sample. This is especially true if repetitive samples need to be taken to follow a trend or reaction. Large samples are also slower to process and involve exposing fragile biological entities to inhospitable environments during the process.

As mentioned earlier existing affinity processes involve removal of the target from the capture entity as the final step. This requires empirical discovery of conditions which will perturb the binding without damaging the desired purified moiety. This can be extremely difficult for example with antibodies where strong binding is often particularly desirable. Obviously the stronger the binding the more denaturing the eluting solution. Sometimes numerous combinations of elutant have to be tried to find a good set of conditions. Sometimes however no combination achieves the right effect.

As well as molecular purifications cells are also used in affinity processes. This can take a variety of forms based on different characteristics of the cells. Usually but not always the cells must be recovered intact from the process for further analysis. Frequently the separation is based on presence of cell surface molecules for which antibodies can be obtained. This can also be combined with size and density measurements. Methods for affinity purification of cells include "Fluorescence Activated Flow Cytometry" which can combine size with the existence of one or more cell surface markers. The problems of cell purification are severe due to their fragility and if antibody selection has been used the selected cells have to be used with the label still attached.

Many areas of science use natural affinities for binding. In genetics complementarity of nucleic acids is commonly utilised as the basis of a method of analysis. For example mRNA is isolated by virtue of the fact that it always has a tail of adenine nucleotides at the end which can be bound to a row of thymidine nucleotides.

Specific gene nucleotide sequences can be captured by the complementary nucleotide sequence. These hybrids can usually be removed very easily by reducing the ionic strength of the elutant allowing the natural charge-driven repulsion between DNA strands to take effect.

As mentioned earlier, sometimes elution conditions cannot be found to remove without damage. This can be turned into an advantage however if the capture is done in the situation where it can act as the linker immobilising the desired activity in place so that subsequent steps can be performed in situ. For example this could be an enzyme reaction in the new science of biotransformations which uses immobilised enzymes for chemical synthesis.

If it is essential to remove the target material then a final resort is to use a membrane material which is itself soluble in a solvent not damaging to the target. This case however does release the capturing material also.

Frequently the coupling of the material to its solid phase would be by covalent linker to avoid any problems of the leaching out of the capture moiety leading to contamination of the process.

If removal of the target moiety is difficult or unnecessary, analytical work can be done in situ. Many biological analyses can be performed on membranes. For example one item is immobilised on the membrane and used to capture the other. Using further labelled binding moieties the presence of an entity can be revealed using fluorescent markers or colourimetric enzyme markers or radiolabels. These can be visualised by eye, by machine or by microscopic analysis or counted by appropriate instrumentation. The requirement for being on a membrane is to allow efficient washing as well as to provide for information of localisation.

Other processes are now carried out on membranes such as enzyme reactions, gene amplification reactions, chemical syntheses etc.

Often the results of a separation especially if it involves cells must be verified by direct observation. This is used to tell whether the cells are still in good condition, whether the separation looks "clean" etc. Sometimes further specific tests must be done on the separated cells to verify their identity by a different route such as specific staining or enzyme activity. If a cell sorter has been used then the produced cells can be examined. If a column has been used they must be eluted to be observed. If however a membrane has been used they can be visualised directly as most membranes are semi-transparent or translucent.

Most capture-based techniques still utilise the column format. This requires the sample to be slowly trickled over the matrix and then washing to be done by trickling over the matrix a succession of washing steps. To improve the washing and the elution, gradients of solvents are often used with varying pH, ionic strength and hydrophobicity.

Also several changes of small volumes of wash solution are far more efficient than one large one which is difficult to implement in a column situation without extending the time further.

These processes can take a long time especially if the binding affinity is weak and sometimes requires the circulation of the sample solution over and over the capture surface to maximise contact. During this long time many constituents will deteriorate and possible denature and consequently many of these processes are now carried out in cooled rooms. These are very unpleasant environments to work in and only partially solve the problem.

One solution to this has been the development of HPLC techniques which among their other characteristics are faster, as the liquids are transferred under pressure. These systems are expensive however and subject the substances to high pressures as well as temperature.

Membrane capture processes are usually faster and therefore better for labile materials but they suffer from problems of dead space which means that the smallest samples cannot easily be used and that the material eluted is lower in concentration.

As existing cartridges are contained, it is not easy to see when they are full of liquid and this can result in air being drawn through and partial drying out of the membrane in an attempt to reduce the minimum volume. Also, because the membranes are contained and supported it is not easy to remove the membrane for visualisation either by light electron microscopy. Similarly they cannot easily be used for subsequent reactions. Some of the cartridges can be disassembled and hence the membrane removed. The true purpose of this is re-use of the cartridge however and usually results in some damage to the membrane.

In some samples the desired constituent is present in minute amounts or numbers. This results in large volumes being drawn over the capture moieties. In addition to the time involved this has the additional disadvantage that the process of liquid flowing in some cases is sufficient to cause the removal of hitherto bound components. The severity of this depends on the nature and strength of the binding, but as biologically significant affinities are often subtle there are many cases where this method of purification cannot be achieved for these reasons.

Another route to solving these problems is to increase the amount of available capture partner by increasing the amount of solid phase. This results in slower flow rates, longer reaction time and greater dilution of the desired material.

Samples for these types of purifications are often clinical and potentially infective and the washing and especially eluent chemicals are also frequently of a hazardous nature. They may be organic solvents, acids, ion-pairing molecules, chelators, detergents etc. Traditional processes using columns offer the potential of injury to the operators as they are exposed to the whole system which often involves the use of significant amounts of the hazardous material. Membrane cartridge devices are better but still rely on squirting out liquids with possibilities for spillages and aerosols.

Many targets once purified will be used in further analysis such as electrophoresis or reactivity for example. For most of these subsequent reactions the target, which is usually in limiting amounts, is preferably at a high concentration. For column and membrane affinity systems, elution will result in the sample being collected at less than maximal concentration. This frequently means that concentration has to be performed before further work can be done. The concentration of a highly purified substance at low starting concentration is very inefficient often leading to losses in excess of 50%.

These small amounts of dilute material also suffer from the disadvantage of being easily denatured on storage and usually have to be mixed in with other molecules such as bovine serum albumin to increase their stability. This defeats some of the object of purifying them in the first place. They are also very liable to adsorb to the surfaces of their storage vessels which sometimes necessitates pre-treatment with toxic silicon compounds (silanes) as a prevention.

As mentioned earlier most chromatographic procedures are reached empirically and frequently involve multiple stages. Strategies are designed by the individual testing of single steps under a variety of conditions on a small scale to optimise both the type and order of steps sometimes for subsequent large scale operations.

This usually means that large numbers of a variety of small columns have to be made, equilibrated, and run both singly and in combination and the elution analysed and monitored. Constituents often need to be radio-labelled to be able to detect them in such processes and this results in a considerable amount of radio-active waste. There are automated systems to perform these reactions but they are very expensive, complex to run and the produced materials still need to be analysed.

The concept of having a separation on the end of a tip has been utilised before in patent specification No. W08809201. In this case however the tip contains column material between two frits and is therefore a miniature column. Usage of the column is by solution flowing by gravity as commonly employed for column processes.

THE INVENTION

This invention provides a device for capturing a component present in a fluid, comprising a pipette tip having an open rearward end adapted to be fitted on a pipette for drawing fluid into the pipette tip, an open forward end, and at least one membrane extending across the pipette tip at or adjacent its forward end.

The membrane is preferably porous, since it is necessary that the fluid be able to flow through, over or round the membrane and into the pipette tip. Preferably the membrane is a woven or non-woven mesh of fibres, which term is used to include threads and filaments which may be discrete or continuous. The membrane may be a mesh weave, a spun bonded mesh, a nuclear track etched membrane, or an electrolytic mesh. Membranes of various pore sizes are possible; it will be understood that the membrane is not normally used simply as a filter to physically separate from a fluid particles that are too large to pass through the pores. Membrane pore size is chosen rather to ensure intimate contact between the fluid and the membrane. The larger is the pore size, the easier is passage of fluid through the membrane but the lower is the capture efficiency of the membrane for the desired component.

Preferably the membrane is adapted to bind and thereby capture a component present in the fluid. For example, the membrane may incorporate a specific binding partner of the component to be bound. The membrane may incorporate capture entities which are ion exchange molecules, affinity proteins such as anti-bodies or biotin-binding molecules, enzymes, nucleic acids, nucleotide oligomers, cell attachment molecules, receptors, chelators etc.

In one embodiment, the membrane is of a material which is capable of binding DNA, for example by chemical interaction or hydrophobic bonding or physical absorption or by a charge interaction. DNA binding to plastics materials is complex and involves various combinations of these phenomena. For example a highly charged polymer surface may favour charge interaction, while an uncharged polymer surface may favour hydrophobic bonding.

Many materials are known which have nuclear capture properties, including polyester, polyamide, polycarbonate, cellulose, nitrocellulose, polyvinylidine difluoride, and glass. Alternatively, the membrane can be made of any material which can be activated, chemically or physically in such a way that it binds the component to be captured. Immobilization of the capture entity, e.g. antibody or other specific binding species, on the membrane is readily effected by a variety of chemical and physical means which are well described in the literature.

The membrane may be chosen with a view to the specific requirements of the separation involved. For example, the membrane may be chosen to be non-inhibitory to subsequent enzyme reactions or culture requirements. The membranes can also be selected to be non-fluorescent, transparent, heat or chemical-resistant.

Capture membranes which have been used successfully are 1, 5, 6 and 11$\mu$m polyester woven membranes and 1 $\mu$m nylon woven membrane. Either 1 $\mu$m membrane is preferred. Less preferred but effective to a lesser extent are 50, 100 $\mu$m random mesh polycarbonate membranes and 5, 10 $\mu$m track-etched polyester membranes. Also 0.45 $\mu$m nitrocellulose has been used successfully, as has 0.45 $\mu$m nylon, although the flow rate and hence washing efficiency were reduced (see Example 1).

It is an advantage of the invention that the desired component is captured on or at or in the forward-facing surface of the membrane. The membrane is mounted at or adjacent the forward end of the pipette tip, that is to say, close enough to the forward end to be easily visible or accessible for subsequent treatment, reaction or analysis. The membrane is preferably bonded to the forward end of the pipette tip, either at right angles to the axis of the pipette tip or set obliquely (i.e. not perpendicular to the longitudinal axis of the pipette tip). An oblique mounting increases the surface area of the membrane, for a given tip diameter and may help to avoid contamination when the device is inserted into a dirty solution. Or the membrane may be mounted on the forward end of a short tubular section, the back end of which is a friction fit on the forward end of the pipette tip of the invention. Several tubular sections comprising several membranes may be mounted on the pipette tip in this way.

The first (or only) membrane is preferably bonded to the pipette tip at or adjacent its forward end. The membrane may be made peelable from the pipette tip for subsequent processing. But in this embodiment it would not be practicable to replace the same or another membrane on the pipette tip. The device of the invention is thus designed to be disposable rather than re-usable.

Alternatively, the membrane may be secured to the forward end of the pipette tip by means of a securing collar.

The pipette tip is preferably a one-piece moulded structure preferably formed of a plastics material, which should withstand autoclaving (a 120° C. for 20 minutes) as well as repeated heating and cooling between 95° and ambient. No mould release or plastizer should be used in the manufacture of the pipette tip, and the plastics material should not inhibit enzyme reactions such as PCR either by removal of crucial components by adsorption or by chemical inhibition. Preferred plastic membranes include polycarbonate, polypropylene, nylon, polyester, PTFE. Polycarbonate and polyester can have the advantage that the tube is transparent. The pipette tip should preferably not fracture on freeze-thawing.

The pipette will usually be an adjustable volume or non-adjustable volume disposable tip micropipette, as produced by Companies such as Gilson and Eppendorf, and well known to those working in biological laboratories. Preferably the rearward end of the pipette tip is internally tapered so as to be a friction fit on a micro pipette. The rearward end of the pipette tip may carry external axial reinforcing ribs.

Preferably the pipette tip is of a brittle plastics material and has between its ends a circumferential line of weakening, e.g. provided by an external groove, along which the tip can be broken manually. The length of the forward end of the tip may be chosen to enable it, complete with the membrane, to be inserted in an eppendorf tube for further processing in such a way that the lid can be shut. The pipette tip is preferably conical, with the rearward end sized to fit a micro pipette, with the tip decreasing in both internal and external diameter towards its forward end.

The small diameter of the end of the tip allows the membrane to be immersed in very small samples. The tip is adapted to contain the fluid that is drawn into it by the pipette, thus avoiding any contamination of the pipette itself. This also allows liquid to be taken up into the tip past the membrane with very little required force. This also allows the liquid to be forced out again past the membrane and hence double the interaction of the sample with the capture partner. This can be repeated any number of times pipetting up and down so the sample has multiple chances to interact with the capture entity. The speed of pipetting can be varied easily or for very slow kinetics the tip could be left incubating in the solution. Once the binding step has been allowed the tip is easily transferred to the required number of washing solutions in turn pipetting up and down each time as required. Several consecutive small volume washes are much more effective in washing terms than the same volume once. This method therefore minimises the required amounts of wash solutions whilst maximising the washing effect. The pipetting for washing can be as vigorous and numerous as desired.

A particular advantage is that the presence of the membrane at the end of the tip results in any entities attaching by whatsoever means to the membrane do so predominantly on the external surface. This is important for any visualisation purposes, for efficient elution or for subsequent reactions or for example cellular entities they can continue to be cultured in situ on the membrane.

The nature of the fluid, containing a component to be captured, is not material to the invention. The fluid may, for example, be a biological fluid such as a body fluid.

In some cases, the fluid may be so "dirty" by virtue of containing so much insoluble matter, that the step of sucking it through the membrane would be slow or difficult. In this case, it may be sufficient to bring the fluid into contact with the outer surface of the membrane without applying any positive or negative pressure through the pipette tip. As the fluid is stirred in contact with the pipette tip, the membrane captures the desired component. The pipette tip can then be removed from the "dirty" fluid, and immersed in a washing fluid which is sucked into the pipette tip and then ejected through the membrane, usually several times.

For applications where many conditions need to be tried for optimal purification perhaps for a subsequent large scale scheme, trial of many conditions can be performed in rapid succession. For multiple preparations the tips can be utilised with a multi-channel version of the micropipette such as are common among those experienced in the area. These commonly allow 8 or 12 purifications to be done simultaneously. The membrane-ended tips can be manufactured attached in a row for easy attachment to the multi-pipettes.

For particularly difficult separations or ones where different components need to be removed from the same sample multiple layers can be used separated by a small spacer. Each of these layers can be derivatised differently so the sample contacts all of them and they could be assembled in a head-to-tail manner. This is also useful where samples are undesirably particulate or otherwise contaminated and the first layer can be chosen to remove some of this unwanted material.

These layers can be used either to remove multiple specific contaminants to improve the separation by capturing the target on two or more layers of the same materials to capture different materials simultaneously or to remove one material while capturing another. The layers can then be separated after treatment by "unslotting" them.

This can be extended to include membranes which have attached to them molecules or entities which are preservatives or enzyme inhibitors to help the desired material to survive. They can also have detergents, surfactants or anti-bacterial agents available on the solid phase membrane which allows their activity to be utilised without contaminating the sample.

An additional variant of this is to have an enzyme activity attached to a section of membrane so that the enzyme can perform its reaction and can then be removed from the sample to avoid sample contamination. In some cases these sections can be stored for re-use.

Reference is directed to our European patent application 92 308 537.7, filed on 18 Sep., 1992 and entitled "Capture Method and Device". That invention describes a method of separating components of cells, which method comprises a) treating a fluid containing whole cells so as to selectively lyse the cytoplasmic membrane together with a small proportion of the nuclear membranes but leaving a large proportion of the cell nuclei intact, b) applying the treated fluid to a surface whereby a mesh of DNA from the lysed nuclei is formed on the surface and captures intact cell nuclei, c) washing the DNA mesh on the surface to separate the captured cell nuclei from other components of the cells.

The said patent application also describes a device for use in the method. The device of the present invention is very suitable for that purpose; the forward-facing surface of the membrane herein described can constitute the surface to which the treated fluid is applied in step b) above. In that case however the membrane would usually not be derivatised.

Reference is directed to the accompanying drawings, in which:

FIGS. 1 and 2 show sectional and end elevations respectively of a preferred form of the device.

FIGS. 3, 4 and 5 are perspective sectional side views of three different devices according to the invention.

FIG. 6 is a perspective sectional side view of such a device in position in an eppendorf tube.

Figure 7:
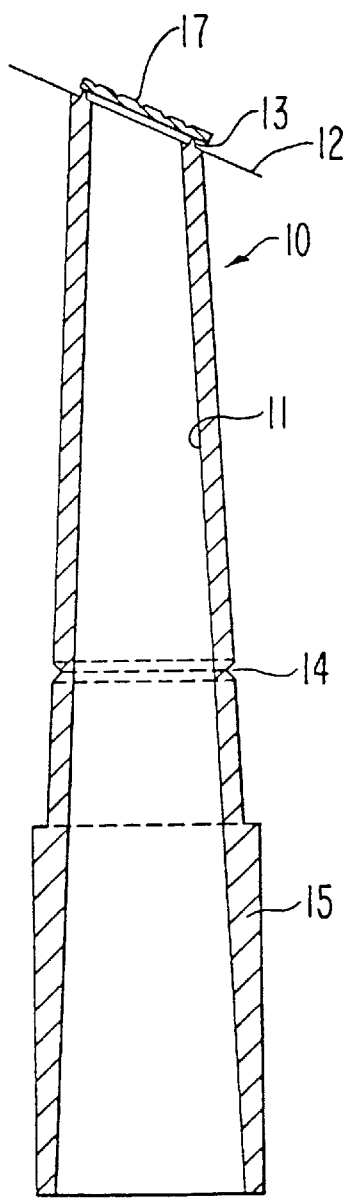
FIG. 7 shows a sectional elevation of an alternative form of the device.

Referring to FIGS. 1 and 2, the device comprises a pipette tip 10 the bore 11 of which decreases in diameter along its length from its rearward end towards its forward end 12. The forward end face of the pipette tip has an annular pip 13 for the attachment of a permeable membrane 17 extending across the bore and selected according to the nature of the component to be captured. The pip has in this construction a triangular cross-section. A line of weakening in the form of a peripheral groove 14 is formed in the wall of the pipette tip at a selected distance from the forward end. In its rearward end portion 15 the external surface of the pipette tip is cylindrical and has a series of axial stiffening ribs 16 to enable that end of the pipette tip to be secured in a friction fit on the end of a micro-pipette. The pipette tip is made from a transparent and brittle thermoplastic plastics material. Polycarbonate is particularly suitable for this purpose.

In use of the device, a biological fluid is drawn into the pipette tip by a micro-pipette through the membrane which captures a component of the fluid. The captured component is then washed by drawing a wash solution through the membrane. The pipette tip is then broken at the line of weakening and the whole forward end part of the pipette tip with the membrane and captured component is placed in a standard eppendorf tube for further treatment. To enable the lid of the eppendorf tube to be closed it is particularly advantageous for the groove 14 to be formed at a distance of 18mm from the forward end of the pipette tip.

FIGS. 3, 4 and 5 show generally similar embodiments. In FIG. 3, a capture membrane 17 is shown extending across the forward end 12 of the pipette tip. An aerosol filter 18 is mounted in the pipette tip between the fracture point 14 and the rearward end 15; the purpose of the filter being to preserve the tip of the micro-pipette from contamination with biological fluid being sucked through the capture membrane.

In FIG. 4 the pipette tip does not carry any membrane bonded thereon. A tubular portion 19 carries a membrane 20 at its forward end; its rearward end is a friction fit over the forward end of the pipette tip.

In FIG. 5, the device is as shown in FIG. 3, with two tubular sections 19 and 21 pushed over and a friction fit on the forward end. The device thus has three membranes, 17, 20 and 22, and the biological fluid is sucked through these in sequence.

FIG. 6 shows a device similar to that illustrated in FIG. 3, inserted into an eppendorf tube 23. The device includes an external peripheral disc 24, just forward of the fracture point 14, which serves as a fracture fulcrum. The membrane 17 is secured to the forward end of the pipette tip by a securing collar 25 which also acts as an anti-reflux seal. The eppendorf tube contains 50 µl of reaction fluid 26 for further treatment of the capture membrane.

In use, sideways pressure is applied to the rearward end 15 of the pipette tip, e.g. in the direction marked by the arrow 27, to break the pipette tip at the fracture point. The rearward end of the pipette tip is then removed, the lid 28 of the eppendorf tube closed, and the capture membrane 17 further treated as required.

FIG. 7 shows an alternative device in which a permeable membrane 17 is mounted oblique to the axis of the device. This embodiment is otherwise similar to that shown in FIG. 1, and reference numerals correspond to those in FIG. 1.

EXAMPLE 1

Use of Membrane Tips for Affinity Purification of a Cytochrome p450 variant from Two Protein Mixtures a) A mixture of proteins containing the protein cytochrome P450 was obtained as a series of molecular weight markers. These were obtained as an aqueous solution at a concentration of around 1 mg/ml for each protein and consist of P450 (55 kd), ovalbumin (46 kd), carbonic anhydrase (30 kd), trypsin inhibitor (21.5 kd), lysozyme (14.3 kd), aprotinin (6.5 kd), insulin chain A (3.4 kd), & insulin chain B (2.3 kd) in Tris buffer pH 8.0.

b) Phenobarbitone treated rats (Guengerich, F. P. and Martin M. V. Arch. Biochem. Biophys., 205, 365–379, 1980) were sacrificed and the livers removed. Extracts were prepared (Guengerich, F. P. J. Biol. Chem. 252, 3970–3979, 1977) of the microsomes known to contain overexpressed P450 protein. This method involves successive homogenisation and centrifugation steps in a saline solution. The extracts once prepared are stored at −70° C. till required.

Tips were prepared as follows: tips were constructed as described with nylon reinforced nitrocellulose membrane attached across the forward end. Antibody was attached to the surface of the membrane by immersing in 100 µl of a solution of a partly purified polyclonal antibody to P450 (Ryan, D. E. and Levin, W. Pharmac. Ther. 45, 15–239, 1990) 10 mg/ml in 100 mM carbonate buffer pH 9.0 containing 10 mg/ml bovine serum albumin. This was held in the solution for 15 minutes and excess was then washed off in phosphate buffered saline pH 7.0. and stored in saline at 4° C. to avoid drying.

10 µl of the protein mixtures in a) and b) were diluted to 500 µl in phosphate buffered saline (PBS).

Separate tips with antibody-coated membrane attached were then used to aspirate up and down the extracts.

The aspiration was repeated five times. The tips were then transferred to wash solution of 3×5 ml PBS and one aspiration up and down was done in each. The membrane was then peeled off the end of the tip and added to sample loading buffer for PAGE electrophoresis.

The samples were boiled in 20 µl of loading buffer containing SDS, DTT, glycerol and bromophenol blue for 2 minutes. Control samples of extract aspirated through an untreated tip as well as depleted extract after "tipping" were prepared by boiling equal amounts of sample and loading buffer together for 2 minutes.

10 µl of each sample was run on a denaturing 12% PAGE gel at 100 V for three hours and subsequently stained in Coomassie blue fixative to reveal the protein bands.

The first three tracks showed mixture A: 1) Mixture after "tipping": 2) Mixture after "tipping" using a "blank" tip without antibody and 3) Material extracted by antibody-treated tip.

The following three tracks showed 5) Liver extract after "tipping" 6) Liver extract after "tipping" using a "blank" tip without antibody 7) Tip extracted material (the additional material in this track may represent antibody contaminants eluting from the tip membrane. Normal practice would be to perform these reactions using radiolabelled extracts. Contamination from the bound antibody would not then be a problem as it would not be radiolabelled.)

The results demonstrate that the antibody held on the tip has efficiently captured a specific substance from a complex mixture during the rapid aspiration steps.

The captured substances can then be removed from the tip membrane for further study.

The tips themselves are not removing substances non-specifically by absorption to the membrane.

EXAMPLE 2

Use of Membrane Derivatised Tips for Immunoprecipitation of p53 Protein from HeLa Cell Extract a) Tips were constructed as described, with a nylon membrane attached across the forward end. Antibody was attached to the surface of the membrane by immersing the tips in either 500 µl of a solution of purified monoclonal antibody to p53, pAb248 (1), or a solution of purified antibody to Adenovirus E1A, M73, (2) in 100 mM carbonate buffer pH 9.0. This was held at 4° C. overnight. The excess solution was removed and the tips washed in phosphate buffered saline (PBS), pH 7.0. The membranes were then blocked by immersion in 500 µl 3% BSA/PBS for 30 minutes at room temperature. After removing excess blocking reagent and washing in PBS, the tips were immersed in 1 ml HeLa cell lysate.

b) Approximately $10^7$ HeLa cells were lysed in 2 ml of 150 mM NaCl, 1% NP40, 50 mM Tris pH 8.0 for 30 minutes on ice. The liquid was removed for incubation with the derivatised tips.

c) The tips and lysate were incubated on ice for 30 minutes, followed by removal of excess lysate. The tips were then washed with 1 ml PBS, by sucking the PBS into the pipette tip and ejecting it from the pipette tip through the membrane three times. Each tip was then added to a tube containing 40 µl of Laemmli sample buffer (2% SDS, 10% glycerol, 100 mM DTT, 60 mM Tris pH 6.8, 0.001% bromophenol blue). The samples were then boiled for 2 minutes and loaded onto 3 separate tracks of a 10–15% polyacrylamide/SDS gel.

The first two tracks show immunoprecipitation of the p53 protein with tips derivatised with anti-p53 antibody, pAb248. In track 3 (negative control), a tip derivatised with an anti-E1A antibody shows no detectable protein immunoprecipitated as would be expected, since the HeLa cells do not express the Adenovirus proteins.

REFERENCES

1. Yewdell, J. W., Gannon, J. V. and Lane, D. P., J. Virol., (1986), 59, 444–452.
2. Harlow, E., Franza, B. R. and Schley, C., J. Virol., (1985), 55, 553.

We claim:

1. A device for capturing a component present in a fluid, comprising a pipette tip having an open rearward end internally tapered to be a friction fit on a pipette for drawing fluid into the pipette tip, an open forward end, and at least one membrane bonded to and extending across said forward end of the pipette tip, said at least one membrane being a woven or non-woven mesh of fibers, and said pipette tip being frustoconical decreasing in internal diameter towards said forward end.

2. The device as claimed in claim 1, wherein the pipette tip is of polycarbonate material.

3. The device as claimed in claim 1, wherein the pipette tip has a longitudinal axis and the membrane is mounted oblique to the longitudinal axis.

4. The device as claimed in claim 1, wherein the membrane is a nylon or polyester woven membrane.

5. The device as claimed in claim 1, wherein the woven membrane has a mesh size of about 0.45 to 11 µm.

6. A device for capturing a component present in a fluid, comprising a pipette tip having an open rearward end internally tapered to be a friction fit on a pipette for drawing fluid into the pipette tip, an open forward end, and at least one membrane bonded to and extending across the said forward end of the pipette tip, said at least one membrane being a woven or non-woven mesh of fibers and incorporating a specific binding partner of said component to be captured, and said pipette tip being frustoconical decreasing in internal diameter towards said forward end.

7. A device as claimed in claim 6, wherein the pipette tip is of polycarbonate material.

8. A device as claimed in claim 6, wherein the pipette tip has a longitudinal axis and the membrane is mounted oblique to the longitudinal axis.

9. The device as claimed in claim 6, wherein the membrane is a nylon or polyester woven membrane.

10. The device as claimed in claim 6, wherein the woven membrane has a mesh size of about 0.45 to 11 µm.

* * * * *